US00PP31396P2

(12) United States Plant Patent
Hansen

(10) Patent No.: US PP31,396 P2
(45) Date of Patent: Jan. 21, 2020

(54) ***HEUCHERA* PLANT NAMED 'CHERRY TRUFFLES'**

(50) Latin Name: ***Heuchera* hybrid**
Varietal Denomination: Cherry Truffles

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,002

(22) Filed: Sep. 10, 2018

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80; A01H 5/02
See application file for complete search history.

*Primary Examiner* — Keith O. Robinson

(57) ABSTRACT

The new and distinct hybrid of *Heuchera* plant named 'Cherry Truffles' with large sinuate foliage with rounded apices and lobes, leaf blades begin the season bright red and develop to deep cherry mahogany without silver overlay surrounding the veins. Branched panicles are deep burgundy displaying bright pink calyces and pale pink petals for about five weeks beginning late spring and repeating through the summer. The new plant is vigorous and produces large clumps with many large leaves.

1 Drawing Sheet

Botanical denomination: *Heuchera* hybrid.
Variety denomination: 'Cherry Truffles'.

BACKGROUND OF THE INVENTION

The present invention relates to a new and distinct cultivar of Coral Bells in the Saxifragaceae family and given the cultivar name of 'Cherry Truffles'. *Heuchera* 'Cherry Truffles' was hybridized by the inventor on Feb. 16, 2015 at a wholesale perennial nursery in Zeeland, Mich., USA. The seed or female parent was 'Inheuredfu' U.S. Plant Pat. No. 25,648 and the pollen or male parent was a proprietary unreleased hybrid known as 13-700-1 (not patented).

*Heuchera* 'Cherry Truffles' was first selected in the fall of 2016 and passed final evaluation in the fall of 2017 from among many other seedlings from the same cross and hundreds of other crosses and assigned the breeder code 15-55-4 through the remaining evaluation process. *Heuchera* 'Cherry Truffles' has been asexually propagated by division at the same nursery in Zeeland, Mich. in 2016 and by sterile, shoot-tip, tissue culture propagation, and the resultant plants have remained stable and continued to exhibit the same characteristics as the original plant for multiple generations.

No plants of *Heuchera* 'Cherry Truffles' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

The nearest comparison varieties include: the female parent 'Inheuredfu', 'Midnight Ruffles' U.S. Plant Pat. No. 25,605, 'Berry Marmalade' U.S. Plant Pat. No. 23,285, 'Crimson Curls' U.S. Plant Pat. No. 13,729 and 'Peach Flambe' U.S. Plant Pat. No. 17,195. 'Inheuredfu' is slower growing and has more coppery colored foliage with less bright reddish coloration in the spring. 'Midnight Ruffles' has foliage that is more greyed and less reddish, the lobes are deeper incised and the margins are more ruffled. 'Berry Marmalade' has more silver overlay on the leaf, the leaves are smaller and do not develop the bright reddish color before flowering of the new plant. 'Peach Flambe' has lighter-colored more orangish foliage with whitish flowers. 'Crimson Curls' has smaller, deep-green foliage coloration that is more deeply dissected and more finely sinuate, and the flowers are cream-colored. The male parent had more reddish foliage, was more rounded and not as ruffled in the leaf blade. *Heuchera* 'Cherry Truffles' differs from its parents as well as all other coral bells known to the applicant in the following combined traits:

1. The large sinuate foliage has rounded apices and lobes.
2. Leaf blades begin season bright red and develop deep cherry mahogany without silver overlay surrounding the veins.
3. Leaf blades are shallowly dissected with apices rounded and apiculate.
4. Flowers provide a bright pink effect from calyces with pale pink petals.
5. Compact, densely-branched panicles of deep burgundy display flowers just above foliage beginning late spring with repeating panicles through the summer.
6. The new plant is vigorous and produces large clumps and many large individual leaves.

BRIEF DESCRIPTION OF THE DRAWINGS

The photographs of the new plant demonstrate the overall appearance of the plant including the unique traits of a plant in a full sun trial block in Zeeland, Mich. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
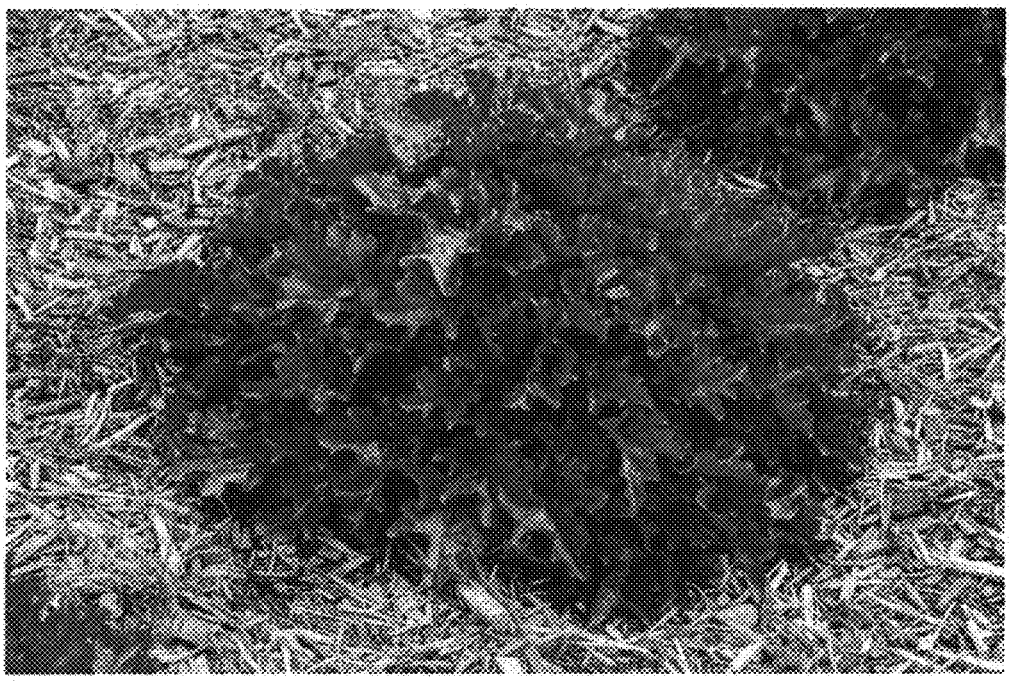
FIG. 1 shows a two-year-old plant with spring foliage before flowering.
Figure 2:
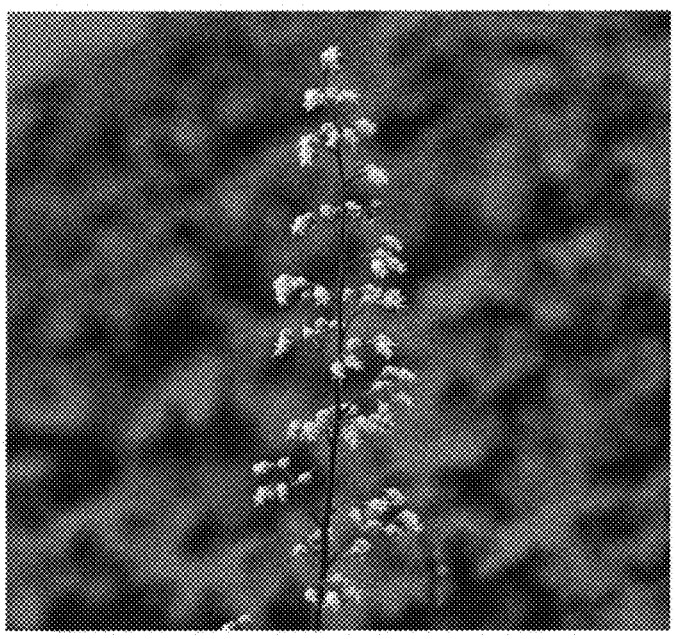
FIG. 2 shows a close-up of a flower panicle with buds and flowers from a two-year-old plant.

The following description is based on a two-year-old plant growing in a partially shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was 'Inheuredfu', the male or pollen parent was the proprietary unreleased hybrid known only by the breeder code 15-55-4 (not patented) with 'Cherry Cola' U.S. Plant Pat. No. 22,967, 'Hercules' (not patented), 'Dark Mystery' (not patented) and 'Fire Chief' U.S. Plant Pat. No. 21,880 in the ancestry;

Plant habit: Hardy herbaceous perennial with basal rosette of foliage; mounded foliage about 30.0 cm tall and 63.0 cm in diameter with scapes to about 52.0 cm long; with 10 stems per plant to about 6.0 cm long and 1.5 cm diameter at base, with medium leaf density, about 18 to 22 leaves per stem;

Roots: Fibrous, finely branched;

Growth rate: Rapid, rooting from cutting in two weeks and finishing in three-liter container in about two and a half months;

Foliage: Cordate to nearly rounded; minutely sparsely puberulent adaxial and abaxial; palmately shallowly lobed with five main lobes dissected less than one-third of the way to petiole; apex and lobe apices rounded, base cordate to auriculate with basal lobes nearly overlapping to overlapping about 0.5 cm; margins crenate to mucronulate, ciliolate; lustrous adaxial and abaxial, strong glossiness; held nearly horizontal; margin sinuate;

Leaf blade size: To about 12.5 cm wide and 12.5 cm long, average about 10.5 cm wide and 11.0 cm long;

Leaf color: Spring and young emerging leaves adaxial nearest RHS 183B with no silver and dark green marbling surrounding the veins, spring young emerging leaves abaxial nearest RHS N186D; mature mid-season leaves adaxial nearest blend of RHS N189A, RHS N187A and RHS 187A without lighter marbling or darker colors surrounding the veins, abaxial mature mid-season leaves nearest RHS 187B; fall and winter color adaxial variable, nearest RHS 147A, N187A and RHS 187A without lighter marbling or darker colors surrounding the veins, fall and winter color abaxial blend between RHS N186C and RHS N187A;

Leaf quantity: Dense, about 180 per plant;

Veins: Palmate, hirsutulous abaxial and adaxial; costate abaxial, slightly impressed adaxial;

Vein color: Emerging or early spring adaxial nearest RHS 183B with emerging spring abaxial nearest RHS N186D; mid-season and flowering time adaxial nearest RHS 183C, mid-season and flowering time abaxial nearest RHS N186C; fall adaxial variable, nearest RHS 189A toward petiole and distally becoming nearest RHS N187A, fall abaxial midrib base nearest N170C with distal and secondary veins becoming nearest RHS 187A;

Petiole: Terete, base amplexicaul; with pubescent hairs to about 2.0 mm long; to about 21.0 cm long and 5.0 mm wide before average about 16.0 cm long and about 3.0 mm diameter above stipule and 7.0 mm at base including stipule;

Petiole color: Emerging leaf nearest RHS N186D; flowering season mature leaf nearest RHS N186C; autumn season nearest RHS 183B with undertone of nearest RHS 177B;

Stipule: Flared at base of petiole; glaucous abaxial and adaxial; margin ciliolate; to about 2.0 cm long and about 1.2 cm wide at base; with two lateral projections of about 3.0 mm long in distal portion;

Stipule color: Young expanding leaf adaxial and abaxial nearest RHS N186D; mature leaf adaxial nearest 187B, abaxial nearest RHS N186D;

Peduncle: Panicle; terete; stiff; pubescent; upright; densely branched; to about 52.0 cm long and 4.5 mm diameter at base, average about 50.0 cm tall and 4.0 mm diameter; about ten per plant with up to about 385 flowers per panicle, average about 310; tightly-branched panicle with up to 28 branches up to 12.0 cm long and 1.0 mm diameter decreasing distally, average 24 branches per panicle; lower branches mostly upright becoming drooping distally; with about three cauline leaves about 2.5 cm apart before flowers and subtending branches; flower density heavy;

Cauline leaves: Palmate; incised margins to shallowly lobed; rounded with mucronate apex and lobes and truncate base; to 3.5 cm long and 4.0 cm across, decreasing distally; petiolate; petiole to 2.0 cm long and 2.0 mm across before stipules; stipules to 6.0 mm long with free distal appendage to 2.0 mm long;

Cauline leaf color: Adaxial blade nearest RHS 187A, abaxial blade nearest RHS 187B; petiole nearest 187A; stipule nearest RHS N186D adaxial and abaxial;

Flowering longevity: Panicle effective for about four to five weeks; individual flowers about 5 days; self-cleaning; sparse density;

Peduncle color: Nearest RHS 187A;

Pedicel: Terete, pubescent; about 3.0 mm long and 0.5 mm diameter; attitude drooping;

Pedicel color: Nearest RHS 187D;

Buds one day prior to opening: Ellipsoid; rounded apex and attenuate base; puberulent to glandular; about 4.0 mm long and 3.0 mm diameter;

Bud color one day prior to opening: Nearest RHS 64B;

Flower: Perfect; campanulate; actinomorphic; about 8.0 mm long to tip of exserted style and 5.0 mm in diameter at corolla face; about 7.0 mm long; color nearest RHS 64B at base and distally between RHS 76C and RHS 76D;

Flower attitude: Drooping;

Calyx: Five, apex rounded, base fused in proximal 3.0 mm to form hypanthium; puberulent to glandular abaxial, glabrous adaxial; about 5.0 mm long and 5.0 mm wide at apex;

Sepals: Five; lanceolate; acute apex, fused in basal 3.0 mm; to about 5.0 mm long and 2.0 mm wide at fusion;

Sepal color: Abaxial nearest RHS 64B, adaxial apex nearest RHS 71A and balance nearest RHS 64B;

Petals: Five; oblanceolate to spatulate; subacute apex and attenuate base; entire; glabrous abaxial; micro-puberulent adaxial base; about 3.0 mm long and 1.0 mm wide in middle;

Petal color: Abaxial and adaxial between RHS 76C and RHS 76D;

Androecium: Five adnate to adaxial sepal about 1.0 mm above base;

*Filaments*.—Five, thin, glabrous; about 2.5 mm long and less than 0.3 mm diameter; color nearest RHS 155B.

*Anthers*.—Ellipsoidal, distinct, basifixed, longitudinal; about 0.7 mm long and about 0.5 mm across; color nearest RHS 17D.

*Pollen*.—Abundant; color nearest RHS 17B.

Gynoecium: One, two-beaked; half-inferior; bifid style with pistil split at ovary; about 7.5 mm long;

*Style*.—Bifid; split apart at apex of ovary; exserted; about 5.5 mm long and about 0.5 mm diameter; color nearest RHS 75B.

*Stigma*.—Acute apex, about 0.1 mm diameter; color nearest RHS 75A.

*Ovary*.—Half-inferior, about 2.0 mm long and 2.0 mm diameter; ellipsoidal to globose, base rounded; color nearest RHS 162D.

Fruit: Small two-beaked capsule; about 2.5 mm long and 2.5 mm across; drying to RHS 200C;

Seeds: Abundant; slightly flattened ellipsoid; about 0.3 mm long, 0.2 mm across and about 0.1 mm thick; color nearest RHS 200A;

Disease and pest tolerance: The new plant grows best with ample moisture and drainage in either part sun or full shade. Cold hardy from USDA zones 4 to 9. The new plant is resistant to high heat. Other resistance and tolerance, including the genus and species of diseases, outside of that normal for *Heuchera* is not known.

It is claimed:

1. A new and distinct coral bells plant named *Heuchera* 'Cherry Truffles' as herein described and illustrated.

* * * * *